United States Patent [19]

Murphy et al.

[11] Patent Number: 4,873,378
[45] Date of Patent: Oct. 10, 1989

[54] PROCESS FOR MAKING 1,3-DIOLS FROM EPOXIDES

[75] Inventors: Mark A. Murphy, Corpus Christi; Brad L. Smith, Portland; Adolfo Aguilo'; Kwoliang D. Tau, both of Corpus Christi, all of Tex.

[73] Assignee: Hoechst Celanese Corporation, Somerville, N.J.

[21] Appl. No.: 133,116

[22] Filed: Dec. 15, 1987

Related U.S. Application Data

[63] Continuation-in-part of Ser. No. 898,072, Aug. 20, 1986, abandoned.

[51] Int. Cl.⁴ .................... C07C 29/36; C07C 31/20

[52] U.S. Cl. .................... 568/867; 568/811; 568/832

[58] Field of Search .................... 568/867, 832, 811

[56] References Cited

U.S. PATENT DOCUMENTS 3,463,819 8/1969 Smith et al. .................... 568/867
3,687,981 8/1972 Lawrence et al. .................... 568/867

*Primary Examiner*—J. E. Evans
*Attorney, Agent, or Firm*—D. R. Cassady; W. E. O'Brien

[57] ABSTRACT

A process for manufacturing 1,3-glycols is disclosed. The process comprises reacting an epoxide with synthesis gas in the presence of rhodium and a phosphine.

28 Claims, No Drawings

PROCESS FOR MAKING 1,3-DIOLS FROM EPOXIDES

REFERENCE TO PRIOR APPLICATION

This application is a continuation-in-part of application Ser. No. 898,072; filed Aug. 20, 1986, now abandoned.

BACKGROUND OF THE INVENTION

This invention relates to the manufacture of 1,3-diols from an epoxide. In one embodiment, this invention relates to the manufacture of 1,3-propanediol from ethylene oxide.

Glycols in general are valuable chemical compounds which find a wide variety of utilities. Such compounds are used, for example, as chemical intermediates in the manufacture of esters, as well as in the synthesis of polyesters. 1,3-Propanediol (1,3-PDO), also referred to as 1,3-propylene glycol or trimethyleneglycol, in particular, had been found to be especially useful in a number of applications. Typically, 1,3-propanediol has been prepared by acid-catalyzed hydration of acrolein to form 3-hydroxypropanal which is subsequently hydrogenated to the corresponding glycol. The high cost of acrolein and the relatively low yields obtained in such reactions have not led to commercial processes for production of 1,3-propanediol which are cost competitive with other commercially available diols which in many instances can be substituted for 1,3-propanediol.

The preparation of 1,3-glycols by the hydroformylation of epoxides, utilizing phosphine-modified cobalt carbonyl complexes as the catalyst, is shown in U.S. Pat. No. 3,463,819. In particular, said patent shows the production of 1,3-propanediol by hydroformylation of ethylene oxide, using a tertiary phosphine-modified cobalt carbonyl catalyst. Although high yields (92%) of 1,3-propanediol were claimed to have been produced in diethyl ether solvent, catalyst concentrations were extremely high, the amount of ethylene oxide charged was low, and no indication of reaction times nor reaction rates was specified. This high catalyst concentration may have been necessary because of the limited catalyst turn-over i.e.; 2-4 moles of product/mole of cobalt and phosphine. Yields of 1,3-propanediol were substantially lower in solvents other than diethyl ether.

U.S. Pat. No. 3,687,981 is also directed to a process for manufacturing 1,3-propanediol. However, the process disclosed in the '981 patent employs two separate stages. In the first stage ethylene oxide undergoes a hydroformylation reaction to produce hydroxyethyl hydroxy dioxane which is insoluble in the initial reaction solvent. The dioxane compound is separated from the initial reaction solvent and is subsequently catalytically hydrogenated to form trimethylene glycol. The patent generally discusses the possibility of using as the hydroformylation reaction catalyst, transition metals, particularly those of Group VIII of the Periodic Table, e.g., cobalt carbonyl tertiary phosphine and rhodium carbonyl. However, the examples in said patent are limited to the use of dicobalt octacarbonyl catalyst.

U.S. Pat. No. 3,054,813 is directed toward a process for the production of 3-hydroxyaldehydes or alpha-beta unsaturated aldehydes by the reaction of epoxides with synthesis gas. Said patent shows the use of a cobalt carbonyl catalyst for the hydroformylation of ethylene oxide, but the product which resulted was acrolein.

In an article by Yokokawa et al., Bulletin of the Chemical Society of Japan (Vol. 37, page 677, 1964), there is shown an attempt to hydroformylate ethylene oxide and propylene oxide using a cobalt carbonyl catalyst. In the case of ethylene oxide, the product was overwhelmingly composed of acetaldehyde. Small amounts of acrolein were formed. In the case of propylene oxide, under some conditions reasonable yields of 3-hydroxybutyraldehyde were produced, but the production of 1,3-butanediol is not mentioned.

It is likely that processes which produce 1,3-glycols from epoxides using "hydroformylation" catalysts, produce 3-hydroxyaldehydes as chemical intermediates which can either be hydrogenated to 1,3-glycols in situ, or isolated in some manner (as in the form of the aforementioned hydroxyalkyldioxanes) and then hydrogenated in a separate step. However, 3-hydroxyaldehydes, such as 3-hydroxypropanal, are unusually reactive species and readily undergo a variety of side reactions. In a literature review entitled "New Synthesis With Carbon Monoxide", B. Cornils, *Springer Verlag*, page 131, 1980, it was stated that numerous attempts had been made to subject oxiranes (epoxides) to the hydroformylation reaction to produce hydroxyaldehydes and that on account of the greater reactivity, not only of epoxides, but also of the resulting hydroxyaldehydes, the epoxide hydroformylation generally led to the formation of a mixture of products and thus unsatisfactory yields.

Under the conditions of a hydroformylation reaction, isomerization of ethylene oxide to acetaldehyde (which is sometimes further hydrogenated to ethanol) can occur. Furthermore, if hydroformylation of ethylene oxide to 3-hydroxypropanal is successful, the 3-hydroxypropanal can dehydrate to yield acrolein, which can be hydrogenated to propanal or propanol, or the 3-hydroxypropanal can undergo condensation (aldol) reactions with other aldehyde molecules to give $C_6$ branched aldehydes, which can undergo dehydration and hydrogenation reactions. It is therefore highly desirable that a catalyst for the production of 1,3-propanediol from ethylene oxide should be able to rapidly hydrogenate 3-hydroxypropanal in situ before undesirable side reactions can occur. Such a catalyst would have the economic advantage of producing the 1,3-propanediol product in a single reactor, without the need for a large and expensive apparatus for the isolation and subsequent hydrogenation of aldehydes.

Thus, there remains a need for an effective method for manufacturing 1,3-glycols, especially from epoxides, which process is usable in a commercial manner.

SUMMARY OF THE INVENTION

It has now been discovered that epoxides may be converted into 1,3-glycols by a hydrocarbonylation reaction which uses rhodium as the catalyst. Thus, the present invention provides a process for manufacturing 1,3-glycols of the formula

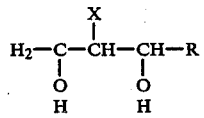

wherein R represents hydrogen, a monovalent aliphatic or aromatic group having from one to about twelve carbon atoms, or a divalent aliphatic group having from 4 to about 6 carbon atoms which together with X forms a cyclic structure, and X represents hydrogen, or if R is divalent, a bond with R. The process comprises reacting an epoxide of the formula

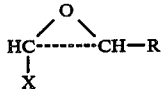

wherein R and X have the aforementioned meaning, with CO and $H_2$ in a suitable reaction solvent, wherein said process is characterized in that the reaction mixture contains (1) an epoxide of the foregoing structure at a concentration from about 0.01 to about 30 weight % (2) rhodium at a molar concentration from about 0.00001 to about 0.1 molar; (3) a phosphine having the formula

wherein $R_1$, $R_2$, and $R_3$ are independently selected from the group consisting of aliphatic and aromatic hydrocarbon groups, the molar ratio of rhodium to phosphine being from about 10:1 to about 1:10; (4) water in an amount from about 0.00 to about 25 weight percent based on the weight of the reaction mixture; (5) CO; and (6) $H_2$; wherein the molar ratio of CO to $H_2$ is from about 10:1 to about 1:10; and (7) an acid and wherein the reaction takes place at a temperature from about 50 to about 200° C. under a pressure from about 200 to about 10,000 psig, for a period of time which is sufficient to form at least some of the desired 1,3-glycol.

Where an acid is used, it is presumed that at least some of the acid and phosphine form a salt in situ. This presumption is strengthened by the discovery that a preformed salt of a phosphine and an acid is substantially equivalent in the reaction of this invention.

Under the conditions in which the concentration of rhodium and phosphine are in equimolar amounts or that the molar concentration of phosphine is less than the molar concentration of rhodium, it has been found that the use of acid is not necessary to the formation of the 1,3-glycol. Under these conditions, acceptable yields of 1,3-propanediol (1,3-PDO) are obtained in the absence of the acid, and in some instances, the presence of high concentrations of acid appears to decrease the rate of formation and yield of product.

In a preferred embodiment of this invention, a salt of an alkali metal cation and a solubilizing anion is also present in the reaction mixture. Typically the salt-cation to rhodium ratio is from about 20:1 to about 1:20.

DETAILED DESCRIPTION OF THE PREFERRED EMBODIMENTS

As indicated above, the process of the present invention provides a method for the manufacture of 1,3-glycols through the hydrocarbonylation of epoxides. The desired glycols therefore contain one more carbon atom and one more oxygen atom than the epoxide. Thus, for example, when the epoxide reactant is ethylene oxide, containing 2 carbon atoms, the resultant 1,3-glycol is 1,3-propanediol, containing 3 carbon atoms. Examples of other specific epoxides which are useful in the present invention include propylene oxide, 1,2-epoxyoctane, cyclohexene oxide, and styrene oxide.

The epoxides, as indicated previously, have the general formula

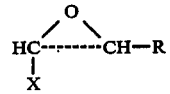

wherein R is hydrogen, a monovalent aliphatic or aromatic group having from one to about twelve carbon atoms, or a divalent aliphatic group having from 4 to about 6 carbon atoms which together with X forms a cyclic structure, and X represents hydrogen or, if R is divalent, a bond with R. R therefore may be a monovalent alkyl group containing, for example, from one to six carbon atoms or may be a divalent alkyl group or an aromatic group, such as a phenyl group. If, for example, R is a divalent alkyl group having four carbon atoms, then the epoxide is cyclohexene oxide. The epoxide is usually present in the reaction mixture at a concentration of about 0.01 to about 30 weight percent. Typically the concentration of epoxide is from about 0.5 to 20 weight percent.

The various epoxides may require different reaction conditions, to achieve optimum results in terms of product yield and selectivity, as well as different specific rhodium, phosphine, or acid components. Using the system comprising rhodium and tricyclohexylphosphine, ethylene oxide gives good product yield and selectivity, and propylene oxide results in good product selectivity. Cyclohexene oxide and epoxyoctane give some products attributable to epoxide carbonylation. Conditions for the latter epoxides may possibly be optimized to achieve better product yield and selectivity.

The carbonylation reaction, as indicated previously, takes place in a suitable solvent. As a general principle, solvents which may be categorized as having medium to high polarity are suitable, such as aromatic solvents, ethers, polyethers, amides, sulfones, and alcohols. Depending upon the reactivity of the particular solvent selected and the specific conditions to be employed, ketones, and esters may also be usable. The preferred solvents generally are high molecular weight ethers, polyethers, and cyclic ethers, especially glycol polyethers. An especially preferred solvent is tetraglyme, the dimethylether of tetraethylene glycol, 2,5,8,11,14-pentaoxapentadecane. Particularly useful solvents also include tetrahydrofuran, diglyme, and Ucon TM oils which are mixed glycol polyethers of ethylene and propylene glycol subunits.

To be suitable, a solvent should solubilize the epoxide reactant. Preferred solvents should not substantially react with any of the components of the reaction mixture or the desired product. Thus, for lower molecular weight epoxides and glycols, solvents such as tetraglyme, tetrahydrofuran and the like are usually used. For higher molecular weight epoxides and glycols, hydrocarbon solvents such as petroleum ethers, toluene, and xylene may be appropriate. The latter solvents are less suitable for lower molecular weight epoxides and glycols such as ethylene oxide and 1,3-propanediol.

The rhodium which is employed in the present process may be introduced in the form of rhodium metal, rhodium salts, and/or rhodium complexes. The only proviso is that the rhodium complex should not contain ligands which insolubilize or poison the catalyst. Thus, selection of the particular rhodium component may, in part, depend upon the solubility of the particular rhodium metal or compound in the specific solvent utilized as the reaction medium. The rhodium useful in the practice of the present invention includes rhodium metal, rhodium oxides, RhI$_3$, RhBr$_3$, RhCl$_3$, Rh(Acac)$_3$, Rh(CO)$_2$Acac, Rh$_6$(CO)$_{16}$, [RhCl(CO)$_2$]$_2$ and Rh(NO$_3$)$_3$, wherein Acac represents acetylacetonate. Likewise, the rhodium useful in the practice of the present invention may be a rhodium carbonyl-phosphine complex which has been preformed, as for example a salt, prior to introduction into the reaction mixture, using any suitable technique for preforming such complexes. The phosphine may or may not be coordinated to the Rh. Typical of such salt-like complexes is bis-ethyltricyclohexylphosphonium hexarhodiumpentadecylcarbonyl.

The concentration of the rhodium in the reaction solvent should be in the range from about 0.00001 molar to about 0.1 molar. Preferably, the concentration of rhodium will be from about 0.005 to about 0.1 molar.

The phosphine which is employed in the present invention has the general formula

$$PR_1R_2R_3$$

wherein R$_1$, R$_2$, and R$_3$ are all independently selected from the group consisting of aliphatic and aromatic radicals. Preferably, R$_1$, R$_2$, and R$_3$ are all alkyl groups containing from about 1 to about 12 carbon atoms. Particularly preferred alkyl groups include methyl, ethyl, n-propyl, iso-propyl, n-butyl, iso-butyl, sec-butyl, and cyclohexyl. Aryl and mixed aryl/alkyl phosphines may be used in the present invention, but their efficacy is dependent upon the particular reaction conditions, including solvent, which is employed. In general, the aryl and mixed aryl/alkyl phosphines are not as efficacious as the trialkylphosphines. The most preferred phosphine is tricyclohexylphosphine. Tri-iso-propylphosphine and tri-isobutylphosphine have also been found to be extremely useful.

The amount of phosphine employed is not critical, but in general, it has been found that a molar ratio of rhodium to phosphine of about 1:1 is preferred. Broadly, a range of about 10:1 to about 1:10 is operable, however. Typically, the molar ratio of rhodium to phosphine will be from about 4:1 to about 1:4.

Under condition where the molar concentration of phosphine is equal to or greater than the molar concentration of rhodium in the reaction mixture, it has been found desirable to add a protonic acid to the reaction mixture. Usually medium or strong acids are preferable for use in the present process. Some acids are, however, less desirable because of their corrosive nature or due to their insolubility in the particular solvent. Halides in particular may promote the decomposition of ether solvents and would be less desirable in such solvents. However, HI and HCl have been found to be extremely useful acids in the process. Preferable acids include phosphoric acid, methane sulfonic, and p-toluene sulfonic acid. Weaker acids such as acetic may be operable, depending upon the particular operating conditions, but may also become esterified under the conditions of the reaction. Suitable acids for the process of this invention include such strong acids as nitric acid, phosphoric acid, hydriodic acid, hydrochloric acid, hydrobromic acid, p-toluene sulfonic acid, and the like. Weak acids suitable for the process include benzoic acid, acetic acid, propionic acid, and the like.

When an acid is used, the amount of acid is desirably in approximately an equimolar amount with the rhodium and/or phosphine. The preferable molar ratio of rhodium to phosphine to acid is approximately 1:1:1. As a general principle, it has been found that variations of the molar ratio by factors of 2-5 only result in mildly deleterious effects. Typically, the molar ratio of acid to phosphine should not be greater than 5:1.

In those instances wherein the molar ratio of phosphine to rhodium is less than 1, the presence of acid, while not causing the reaction to fail, appears to be somewhat deleterious to both the rate of formation and the yield of 1,3-glycol. Consequently, in a preferred embodiment, the presence of acid in the reaction mixture is to be avoided.

The acid may be added to the reaction mixture or a salt of the acid and phosphine may be preformed and added to or substituted for the phosphine or acid constituents in the reaction mixture.

In a preferred embodiment, metal salts, preferably salts of an alkali metal cation, may be added to the reaction mixture. When this salt is added it generally increases the rate of the reaction as shown by an increase in the rate of gas up-take during the reaction. In general, the presence of a salt also decreases the induction period of the reaction. Salt concentrations are not particularly critical to the rate or to the yield of 1,3-diol with the Rh to salt ratio being typically from about 20:1 to about 1:20. Cations may include Li$^+$, Na$^+$, K$^+$, Rb$^+$, and Cs$^+$. The anions comprising the salt must be a solubilizing anions in the solvent under the conditions of the reaction. Typical anions may include F$^-$, Cl$^-$, Br$^-$, I$^-$, NO$_3^-$, benzoate, acetate, sulfonate, and the like.

The ratio of hydrogen to carbon monoxide employed in the hydrocarbonylation reaction should be equal to or greater than 1:1 and preferably no greater than about 5:1, although acceptable yields are realized at concentrations in narrow ranges on both sides of the preferred range.

With respect to the pressure employed during the hydrocarbonylation reaction, the pressure is not critical and generally falls within the range from about 200 to about 10,000 psig. Preferably, the pressure falls in the range of from about 1,000 to about 4,000 psig.

The temperature used in the carbonylation reaction also is not critical. As a general proposition, it has been found that increasing temperature also increases rates. However, increasing temperatures may have an adverse affect on selectivity. Thus, some balancing of temperature is required in order to achieve suitable rates and suitable selectivities. Generally, a temperature of from about 50 to about 200° C. will be employed, preferably from about 100 to about 150 ° C.

For the production of 1,3-propanediol, using the rhodium, tricyclohexylphosphine system, at 2500 psig in tetraglyme solvent, containing 0.69 M water, a temperature of 110° C. results in an efficiency of 85 to 90%, but by increasing the temperature to 130° C., the efficiency is reduced to 70 to 75%. Also, as the temperature increases, the induction period also declines.

As a general proposition with respect to H$_2$:CO composition, reaction pressure, and reaction temperature, all will vary somewhat based upon the particular reaction conditions employed and adjustment thereof is within the ordinary skill of one in the art.

Water, in general, has been found to be useful in conjunction with many catalysts and solvents. In particular, though the presence of water is not necessary for the function of the catalysts used in this invention, in the absence of water, substantial induction periods are sometimes observed between the injection of ethylene oxide and the onset of the uptake of synthesis gas and the production of product, such as 1,3-propanediol. It has been found that the presence of small amounts of water can sometimes substantially decrease the length of the induction periods, and hence shorten the overall reaction times. However, if the amount of water is increased beyond a given level, poorer yields may result. As a broad proposition, from about 0.00 to about 25 wt. % water is employed, preferably from about 0.0 to about 10 wt. %. The amount of water employed, as indicated, to achieve optimum results, will vary depending upon the particular reaction system and conditions employed.

The present invention is capable of achieving yields of 1,3-glycols, such as 1,3-propanediol in excess of 85 percent based upon the epoxide, such as ethylene oxide, and production rates substantially above 1 mol/liter/hour in a single carbonylation reactor. Such results are certainly unexpected and surprising, since the use of rhodium catalysts for the carbonylation of epoxides to 1,3-glycols has not been shown in the prior art. The present results are also surprising in view of the fact that most prior art cobalt catalysts generally only achieved substantially lower rates and efficiencies for precursors of 1,3-propanediol, while the present process provides a high yields, single step process for the production of 1,3-glycols without the need for separate, large hydrogenation reactors for 1,3-glycols precursors.

The present invention is further shown by the following nonlimiting examples.

General Experimental Method Employed in the Examples

All examples were performed in a batch autoclave unit which consisted of a 300 cc Hastelloy autoclave, equipped with remotely operable controls for feeds, vents, stirring, heating, cooling, and the like. Standard stainless-steel tubing and Swagelok fittings were employed at the lower reactor pressures. At pressures of 2500 psig, high-pressure type fittings, valves, and tubings were employed.

All catalysts and solvents were weighed under nitrogen and rapidly charged to a cold autoclave which was then purged twice with nitrogen and twice with synthesis gas. Subsequently, the autoclave was pressurized with synthesis gas to the desired pressure and heated under slow stirring to reaction temperature, over a period of 0.5 to 4.0 hours. Ethylene oxide was then injected into the autoclave from either a pressurized blowcase bomb or a Ruska syringe pump, at which time fast stirring was commenced and the total reactor pressure raised to the final desired value, using synthesis gas to control the pressure. Constant reactor pressures were maintained automatically during the runs by feeding synthesis gas on demand from a high-pressure synthesis gas reservoir of known volume. The uptake of reaction synthesis gas was monitored by periodic measurement of the pressure of the synthesis gas reservoir. Runs were terminated, usually when synthesis gas uptake slowed to nearly zero, by slowing the stirring rate, terminating the synthesis gas feed, and cooling the reactor as rapidly as possible, typically over a 30 to 60 minute period.

Small quantities of ethylene oxide were injected into the reactor which was hot and pressurized, using either a Ruska syringe or a pressurized blowcase bomb by condensation of ethylene oxide vapor, from a lecture bottle, into the blowcase bomb which was chilled to dry ice temperatures. When ethylene oxide had been charged to the blowcase bomb, the blowcase bomb was detached from the transfer apparatus, weighed, then connected to the autoclave.

When the Ruska pump method was used for injecting the ethylene oxide, liquid ethylene oxide was transferred through stainless steel lines to the Ruska syringe pump which then injected the ethylene oxide into the autoclave unit.

Because liquid ethylene oxide became held up in the lines, fittings, and valves leading to the autoclave, it was necessary to charge somewhat larger than theoretical quantities of ethylene oxide to the blowcase bomb or Ruska pump and then calibrate the unit for the quantity of ethylene oxide which actually reached the autoclave. Calibration runs were performed by charging the reactor with 100 grams of water and 1.8 grams of sulfuric acid and heating it to 100° C. Ethylene oxide was then charged to the blowcase bomb or Ruska pump, injected into the reactor, which was then heated for two hours to achieve ethylene oxide hydrolysis to ethylene glycol. The resulting ethylene glycol:water solutions were analyze for ethylene glycol using gas chromatography. In a typical run, 12.0 grams of ethylene oxide would be charged to the blowcase bomb and the ethylene glycol equivalent of 10.0 grams of ethylene oxide reached the reactor. Ethylene oxide feed was then back-calculated from the ethylene glycol and plots of ethylene oxide observed versus ethylene oxide charged, were constructed. Such plots were found to be reasonably linear over the range of 5 to 15 grams of ethylene oxide and typically showed 75 to 85 percent ethylene oxide efficiency in the transfer operation. The results of such calibration runs were then used to calculate ethylene oxide feed for the catalytic carbonylation runs.

With respect to the materials employed in the Examples, [RhCl(CO)$_2$]$_2$, P(C$_6$H$_{11}$)$_3$ and P(n-C$_4$H$_9$)$_3$ were purchased from Strem Chemicals and stored and handled under nitrogen. Rh(CO)$_2$Acac was either purchased from Englehard or prepared from RhCl$_3$·3H$_2$O, acetylacetone, and dimethylformamide and then recrystallized from hexane to yield green-red crystalline needles.

Ethylene oxide (99.7% min) was purchased from Matheson and stored in chilled water. H$_2$/CO mixtures were purchased from Iweco. Tetraglyme and sulfolane were used in the Examples as received from Aldrich, as was the n-butanol which was received from Burdick and Jackson. The toluene and tetrahydrofuran which was received from Aldrich, were distilled from sodium metal under nitrogen.

In the following examples where yields are quoted, yields were calculated from the observed moles of product divided by the moles of EO calculated (via use of the EO calibration procedure) to have been charged to the reactor. In some cases, due to some experimental error in the ethylene oxide injection procedure and the associated calibration procedure, the sum of analyzed products derived from ethylene oxide somewhat exceeded the calculated quantity of ethylene oxide charged to the reactor. In those examples, product efficiencies (which have been normalized to 100% EO accountability) are quoted.

EXAMPLE 1

Eighty grams of tetraglyme, 0.50 gram of Rh(CO)$_2$Acac, 1.1 grams of tricyclohexylphosphine, and 0.1 gram of hydroquinone were charged to a 300 cc autoclave according to standard procedures. The mixture was heated to 100° C. under 1000 psig of 2:1 $H_2/CO$, the reactor pressure then increased to 1400 psig and 8.9 grams of ethylene oxide was injected from a Ruska pump. Uptake of 2:1 $H_2/CO$ gas began in less than 25 minutes, and the pressure was thereafter maintained at approximately 1400 psig by addition of 2:1 $H_2/CO$ on demand. The reaction was terminated after 4.6 hours (gas adsorption had not completely ceased), and the product removed and analyzed by gas chromatography. The product contained no free 1,3-propanediol, but did contain small amounts of 3-hydroxypropanal (0.0016 mole) and 2-hydroxyethyl1,3-dioxane (0.0002 mole). The major products were unconverted ethylene oxide (0.0895 mole), acrolein (0.0112 mole), and 2-methylpentanol (0.0097 mole). Smaller amounts of acetaldehyde, propanol, and 2-methyl pentanal were also detected, along with numerous other small byproducts. This example illustrates that ethylene oxide is carbonylated to $C_3$ products by the use of Rh/phosphine catalysts in the absence of acid promoters. Only small amounts "PDO-precursor" molecules were produced, but substantial amounts of $C_3$ products (which presumably arise from the reaction of EO with CO and $H_2$) are observed. Also, substantial amounts of $C_6$ products (which may arise from the coupling of $C_3$ aldehydes) were produced.

EXAMPLE 2

Eighty grams of tetraglyme, 0.53 gram of Rh(CO)$_2$Acac, 0.54 grams of tricyclohexylphosphine, 1.0 gram of 57% aqueous HI, 5.0 grams of $H_2O$, and 0.1 gram of hydroquinone were charged to an autoclave and heated to 120° C. under 1500 psig of 2:1 $H_2/CO$. Ethylene oxide (8.9 grams) was injected from a Ruska pump and thereafter 2:1 $H_2/CO$ was fed on demand to maintain a 1500 psig pressure. The run was terminated after 116 minutes. The product contained 0.057 mole of 1,3-PDO, 0.014 mole of HPA, and 0.012 mole of 2-hydroxyethyl-1,3-dioxane for a total yield of "PDO Precursors" of 47.4%. Major byproducts included Ethanol (0.045 mole), acetaldehyde (0.019 mole), propanal (0.009 moles), propanol (0.004 mole), 2-methylpentanal (0.006 mole) and 2-methylpentanol (0.005 mole). Traces of ethylene glycol and other unidentified products were also observed. This example illustrates the use of an acid promoter (HI) to improve the activity and selectivity of a rhodium/phosphine catalyst for the carbonylation of ethylene oxide to 1,3-propanediol at relatively low pressure.

EXAMPLE 3

Eighty grams of tetraglyme, 0.54 gram of rhodium trichloride hydrate, 0.53 gram of tricyclohexylphosphine, 0.20 gram of concentrated aqueous HCl, 5.11 grams of $H_2O$, and 0.11 gram of hydroquinone were charged to an autoclave. The mixture was heated to 120° C. under 1000 psig of 2:1 $H_2/CO$, and 9.4 grams of ethylene oxide was injected from a blowcase bomb utilizing 2:1 $H_2/CO$, and the final pressure brought to 2500 psig. Gas uptake began after approximately 50 minutes, and the run was terminated after 3 hours when gas uptake had essentially stopped. The product was found to contain 0.1506 mole of 1,3-PDO and 0.006 mole of HPA, for a combined yield of 73.4%. Major byproducts included ethanol (0.053 mole), propanol (0.017 mole), ethylene glycol (0.013 mole) and ethylene oxide (0.003 mole). Because the apparent yield of EO derived molecules was 114.5%, the ethylene oxide efficiencies were normalized, and showed that "PDO Precursors" were formed with a 64.9% efficiency at a rate of 0.626 moles/liter/hour. This example illustrates that 1,3-propanediol can be produced in reasonably good efficiency from a catalyst precursor which does not contain acetylacetonate ligands. It also illustrates the use of hydrochloric acid promoter.

EXAMPLE 4

Eighty grams of tetraglyme, 0.51 gram of Rh(CO)$_2$Acac, 0.41 gram of tri-isobutylphosphine, 0.14 gram of phosphoric acid, 5.11 gram of $H_2O$, and 0.1 gram of hydroquinone were charged to an autoclave. The mixture was heated to 120° C. under 1000 psig of 1:1 $H_2/CO$, then 10.0 grams of ethylene oxide was injected from a blowcase bomb, and the pressure increased to 2500 psig. Uptake of synthesis gas began after about 40 minutes, and the run was terminated after 3.6 hours when syngas uptake had essentially stopped. Analysis of the product showed the presence of 0.166 mole of 1,3-PDO. Major byproducts included ethanol (0.0184 mole), acetaldehyde (0.0053 mole), ethylene glycol (0.012 mole), propanal (0.006 mole) and propanol (0.011 mole). The yield of 1,3 -propanediol was 74.3% at a rate of 0.567 mole/liter/hour. This example illustrates that 1,3-propanediol can be produced in good efficiency by use of a trialkylphosphine other than tricyclohexylphosphine.

EXAMPLE 5

Eighty grams of tetraglyme, 0.52 gram of Rh(CO)$_2$Acac, 0.54 grams of dicyclohexylphenylphosphine, 0.14 gram of phosphoric acid, 5.1 grams of $H_2O$, and 0.1 grams of hydroquinone were charged to the autoclave and heated to 110° C. under 1000 psig of 2:1 $H_2/CO$. Ethylene oxide (10.1 grams) was injected from a blowcase bomb, and the pressure increased to 2500 psig. Gas uptake began after about 1 hour, and the run was terminated after 6.5 hours. Analysis of the product showed the presence of 0.115 mole of 1,3-propanediol, 0.040 mole of acetaldehyde, 0.027 mole of ethanol, and smaller amounts of acrolein, propanal, propanol, and ethylene glycol. The yield of 1,3-propanediol was calculated to be 50%, at a rate of 0.22 mole/liter/hour. This example illustrates that 1,3-propanediol can be produced in reasonable yields by use of a rhodium catalyst promoted by a phosphine which contains an aryl substituent.

EXAMPLE 6

Eighty grams of tetraglyme, 0.51 gram of Rh(CO)$_2$Acac, 0.53 gram of tricyclohexylphosphine, 0.13 gram of phosphoric acid, 5.0 grams of $H_2O$, and 0.1 grams of hydroquinone were charged to an autoclave and heated to 110° C. under 1000 psig of 2:1 $H_2/CO$. Ethylene oxide (10.2 grams) was injected from a blowcase bomb, and the pressure increased to 2500 psig. Gas uptake began after 50 minutes, and the run was terminated after 4.0 hours. The product contained 0.1905 mole of 1,3-propanediol, 0.0235 mole of ethanol, 0.0154 mole of propanol, 0.0125 mole of ethylene glycol, and 0.0089 mole of ethylene oxide. Because the apparent yield of EO derived molecules was 110%, the ethylene oxide based efficiencies were normalized, and showed that 1,3-propanediol was formed with a 77.5% efficiency at a rate of 0.595 mole/liter/hour. This example illustrates that 1,3-propanediol can be produced in relatively good efficiencies and rates by the use of a rhodium/ phosphine catalyst promoted by water and phosphoric acid.

EXAMPLE 7

Eighty grams of tetraglyme, 0.52 gram of Rh(CO)$_2$Acac, 0.53 gram of tricyclohexylphosphine, 0.13 gram of phosphoric acid, 1.05 grams of H$_2$O, and 0.10 grams of hydroquinone were charged to an autoclave and heated to 110° C. under 1000 psig of 2:1 H$_2$/CO. Ethylene oxide (10.0 grams) was injected from a blowcase bomb, and the pressure increased to 2500 psig. Gas uptake began after approximately 90 minutes, and the run was terminated after 5.5 hours. The product contained 0.1931 mole of 1,3-propanediol, 0.0172 mole of ethanol, 0.0141 mole of propanol, and 0.0029 mole of ethylene oxide. Overall, 1,3-propanediol was produced in 85% yield at a rate of 0.438 mole/liter/hour This example illustrates that 1,3-propanediol efficiencies are somewhat improved when the amount of water is decreased relative to the levels used in previous examples.

EXAMPLE 8

Eighty grams of tetraglyme, 0.52 gram of Rh(CO)$_2$Acac, 0.54 gram of tricyclohexylphosphine, 0.14 gram of phosphoric acid, and 0.10 gram of hydroquinone were charged to the autoclave. No water was added to the charge. The mixture was heated to 110° C. under 1000 psig of 2:1 H$_2$/CO. Ethylene oxide (10.0 grams) was injected from a blowcase bomb, and the pressure increased to 2500 psig. Gas uptake began after approximately 160 minutes, and the run was terminated after 6.5 hours. Product analysis showed the presence of 0.1983 mole of 1,3-propanediol, 0.0166 mole of ethanol, 0.0046 mole of acetaldehyde, and 0.0092 mole of propanol. The yield of 1,3-propanediol was 87% at a rate of 0.377 mole/liter/hour. This example illustrates that 1,3-propanediol can be produced in good yields in the absence of water promoter, though "induction periods" are somewhat longer in the absence of water.

EXAMPLE 9

Eighty grams of tetraglyme, 0.51 gram of Rh(CO)$_2$Acac, 0.54 grams of tricyclohexylphosphine, 0.13 gram of phosphoric acid, and 1.05 grams of H$_2$O were charged to the autoclave. No hydroquinone was added. The mixture was heated to 110° C. under 1000 psig of 2:1 H$_2$/CO and ethylene oxide (10.1 grams) was injected from a blowcase bomb and the pressure increased to 2500 psig. Gas uptake began after about 90 minutes, and the run was terminated after 6.5 hours. Product analysis showed the presence of 0.2172 mole of 1,3-propanediol, 0.0196 mole of ethanol, 0.0133 mole of propanol, and traces of acetaldehyde and ethylene oxide. Because the apparent yield of ethylene oxide derived molecules was 113%, the ethylene oxide efficiencies were normalized, and showed that 1,3-propanediol was produced in 85% efficiency at a rate of 0.41 mole/liter/hour. This example illustrates that the absence of hydroquinone "promoter" (which was included in many of the examples documented here) has no substantial effect on the yields or rates of production of 1,3-propanediol.

EXAMPLE 10

Eighty grams of Ucon TM 50-HB-100 polyglycol ether, 0.52 gram of Rh(CO)$_2$Acac, 0.53 gram of tricyclohexylphosphine, 0.13 gram of phosphoric acid, 5.1 grams of H$_2$O, and 0.1 grams of hyroquinone were charged to the autoclave and heated to 110° C. under 1000 psig of 2:1 H$_2$/CO. Ethylene oxide (10.0 grams) was injected from a blowcase bomb, and the pressure increased to 2500 psig. Gas uptake began after approximately 20 minutes, and the run was terminated after 3.0 hours. Product analysis showed the presence of 0.1775 mole of 1,3-propanediol, 0.0243 mole of propanol, 0.0269 mole of ethanol, 0.0125 mole of acetaldehyde, 0.0102 mole of acrolein, and traces of ethylene oxide and ethylene glycol. Because the apparent yield of ethylene oxide derived molecules was 112%, the ethylene oxide efficiencies were normalized, and showed that 1,3-propanediol was produced in 70.2% efficiency, at a rate of 0.717 mole/liter/hour. This example illustrates that 1,3-propanediol can be produced in good efficiencies in a complex polyglycol ether solvent other than tetraglyme.

EXAMPLE 11

Eighty grams of tetrahydrofuran, 0.52 gram of Rh(CO)$_2$Acac, 0.54 gram of tricyclohexylphosphine, 0.13 gram of phosphoric acid, 5.1 grams of H$_2$O, and 0.10 gram of hydroquinone were charged to the autoclave and heated 110° C. under 1000 psig of 2:1 H$_2$/CO. Ethylene oxide (10.0 grams) was injected from a blowcase bomb, and the pressure increased to 2500 psig. Gas uptake began after approximately 40 minutes, and the run was terminated after 3.5 hours. Analysis of the product showed the presence of 0.2058 mole of 1,3-propanediol, 0.0166 mole of ethanol, 0.114 mole of propanol, and 0.0026 mole of acrolein. Because the apparent yield of ethylene oxide derived molecules was 106%, the ethylene oxide efficiencies were normalized to show that 1,3-propanediol was produced in 85.8% efficiency at a rate of 0.739 mole/liter/ hour. This example illustrates that 1,3-propanediol can be produced in high efficiency in a monoether solvent, and that is extremely unlikely that 1,3-propanediol could be derived from decomposition of solvent.

EXAMPLE 12

Eighty grams of tetraglyme, 0.51 gram of Rh(CO)$_2$Acac, 0.54 gram of tricyclohexylphosphine, 0.14 gram of phosphoric acid, 5.11 grams of H$_2$O, and 0.11 gram of hydroquinone were charged to the autoclave and heated to 110° C. under 1000 psig of 2:1 H$_2$/CO. Propylene oxide (15.8 grams) was charged to a blowcase bomb, and then injected into the autoclave. No attempt was made to calibrate for losses of propylene oxide during the injection procedure. No gas uptake occurred for 7.5 hours, after which the reaction was halted and workup begun. The liquid product was recovered (101.7 grams) and analyzed by gas chromatography (GC) and GC-mass spectra. The product was found to contain approximately 7.8 wt % of unconverted propylene oxide, approximately 5.5 wt % 1,3-butanediol, and approximately 0.5 wt % of 1,2-propylene glycol. No other significant products were detected. Although not optimized, this example illustrates that 1,3-butanediol can be produced via carbonylation of propylene oxide in a relatively selective manner.

EXAMPLE 13

Eighty grams of tetraglyme, 0.51 gram of Rh(CO)$_2$Acac, 0.55 gram of tricyclohexylphosphine, and 1 gram of water were charged to a 300 cc. autoclave according to the standard procedures. The mixture was heated to 100° C. under 2000 psig of 2:1 $H_2$/CO; the reactor pressure then increased to 2300 psig and 10.4 grams of ethylene oxide was injected from a Ruska pump. Uptake of the 2:1 $H_2$/CO gas began in about 2.16 hours, and the pressure was thereafter maintained and approximately 2500 psig by addition of 2:1 $H_2$/CO on demand. The reactor was terminated after 5.5 hours and the product removed and analyzed by gas chromatography. The product contained 0.147 mole 1,3-PDO, 0.009 mole ethanol, 0.032 mole propanol. This example demonstrates that an acid is not needed to obtain good yields of 1,3-PDO when molar equivalents of rhodium catalyst and phosphine ligand are used.

EXAMPLE 14

Eighty grams of tetraglyme, 0.51 gram of Rh(CO)$_2$Acac, and 0.50 gram of tricyclohexylphosphine were charged into a 300 cc. autoclave according to the standard procedures. The mixture was heated to 100° C. under 2000 psig of 2:1 $H_2$/CO; the reactor pressure increased to 2300 psig and 10.4 grams of ethylene oxide was injected from a Ruska pump. Uptake of the 2:1 $H_2$/CO gas began in 3 hours 10 minutes and the pressure was thereafter maintained at approximately 2500 psig by addition of 2:1 $H_2$/CO on demand. The reaction was terminated at 7.5 hours and the product removed and analyzed by gas chromatography. The product contained 0.202 mole 1,3-PDO, 0.013 mole ethanol, 0.007 mole acetaldehyde, 0.007 mole propanol, and 0.007 mole propionaldehyde. This example demonstrates that in the absence of water and an acid, a high yield of 1,3-PDO is obtained when the Rh:P ratio is > 1.

EXAMPLE 15

Eighty grams of tetraglyme, 0.51 gram of Rh(CO)$_2$Acac, 0.42 gram of tricyclohexylphosphine, and one gram of water were charged to a 300 cc. autoclave according to the standard procedures. The mixtures was heated to 110° C. under 2000 psig of 2:1 $H_2$/CO gas. The pressure increased to 2500 psig and 10.2 grams of ethylene oxide was injected from a Ruska pump. Uptake of the gas began in about 5.33 hours, and the pressure was thereafter maintained at approximately 2500 psig by the addition of 2:1 $H_2$/CO on demand. The reaction was terminated after 9.5 hours and the product removed and analyzed by gas chromatography. The product contained 0.210 mole 1,3-PDO, 0.023 mole ethanol, 0.002 moles acetaldehyde, 0.009 mole propanol. This example shows that a good yield of 1,3-PDO can be obtained at a Rh:P ratio of > 1 in the absence of acid.

EXAMPLE 16

Eighty grams of tetraglyme, 0.51 gram Rh(CO)$_2$Acac, 0.28 gram of tricyclohexylphosphine, 0.09 gram of cesium acetate, and 1 gram water were charged to a 300 cc autoclave according to the standard procedures. The mixture was heated to 110° C. under 2000 psig of 2:1 $H_2$/CO; the reactor pressure then increased to 2300 psig and 10.2 grams of ethylene oxide was injected from a Ruska pump. Uptake of 2:1 $H_2$/CO gas began in about one hour and the pressure was thereafter maintained at 2500 psig by the addition of 2:1 $H_2$/CO gas on demand. The reaction was terminated in 6 hours and the products removed and analyzed by gas chromatography. The product contained 0.199 mole 1,3-PDO, 0.024 mole ethanol, 0.003 mole acetaldehyde, 0.007 mole propanol, 0.002 mole propionaldehyde, plus 0.0052 moles C$_6$ byproducts. This example demonstrates the benefit of adding a salt of an alkali metal to the reaction mixture.

EXAMPLE 17

Eighty grams of tetraglyme, 0.51 gram of Rh(CO)$_2$Acac, 0.55 gram of tricyclohexylphosphine, 0.20 gram of lithium acetate, 0.16 gram of phosphoric acid and 1 gram of water were charged into a 300 cc autoclave according to the standard procedures. The mixture was heated to 110° C. under 2000 psig of 2:1 $H_2$/CO; the reactor pressure increased to 2300 psig; and 10.4 grams of ethylene oxide was injected from a Ruska pump. Uptake of the 2:1 $H_2$/CO gas began at 1.1 hours and the pressure was thereafter maintained at approximately 2500 psig by additions of 2:1 $H_2$/CO gas on demand. The reaction was terminated after 6.5 hours and the product removed and analyzed by gas chromatography. The product contained 0.174 mole 1,3-PDO, 0.019 mole ethanol, 0.001 mole acetaldehyde, 0.022 mole propanol, 0.001 mole acetaldehyde, and 0.004 mole of various C$_6$ volatile products. This example demonstrates the addition of a salt and an acid to the reaction mixture.

EXAMPLE 18

Eighty grams of tetraglyme, 0.51 grams of Rh(CO)$_2$Acac, 0.55 gram of tricyclohexylphosphine, 1.06 grams of LiI, and 0.16 grams of phosphoric acid were charged to a 300 cc autoclave according to the standard procedures. The mixture was heated to 110° C. under 2000 psig of 2:1 $H_2$/CO; the reactor pressure then increased to 2300 psig and 10.4 grams of ethylene oxide was injected from a Ruska pump. Uptake of the gas began immediately and the pressure was thereafter maintained at 2500 psig by addition of 2:1 $H_2$/CO on demand. The reaction was terminated at 0.7 hours and the products removed and analyzed by gas chromatography. The product contained 0.098 mole of 1,3-PDO, 0.014 mole 3-hydroxypropanal, 0.059 mole of ethanol, 0.004 mole acetaldehyde, 0.006 mole of propanol, 0.005 moles propionaldehyde, and lesser amounts of other volatile materials. This example demonstrates the present invention in the presence of a salt and an acid but in the absence of water.

EXAMPLE 19

Example 18 was repeated except that 1 gram of water was added to the reaction mixture. Products identified included 0.148 mole of 1,3-PDO, 0.056 mole of ethanol, 0.002 moles acetaldehyde, 0.005 mole of propanol and several minor components. This example demonstrates the presence of water in the reaction mixture which includes a salt and an acid.

EXAMPLE 20

Example 18 was repeated except that 4:1 $H_2$/CO was charged initially. During the progress of the reaction the pressure was maintained with 2:1 $H_2$/CO. The products identified in the reaction mixture were 0.099 mole 1,3-PDO, 0.044 mole ethanol, 0.005 mole 3-hydroxypropanal, 0.002 mole acetaldehyde, 0.008 propanol, and lesser amounts of other products. This example illustrates that a 4:1 $H_2$/CO ratio is useful in the reaction although the ratio of 1,3-PDO to other products is not as favorable as with a 2:1 $H_2$/CO ratio.

EXAMPLE 21

Example 18 was repeated except that 1:1 $H_2/CO$ was charged initially. Thereafter 2:1 $H_2/CO$ was fed to approximate consumption. The products identified in the reaction mixture were 0.074 mole 1,3-PDO, 0.31 mole ethanol, 0.023 mole 3-hydroxypropanal, 0.003 mole acetaldehyde, 0.007 mole propionaldehyde, 0.004 mole propanol, and lesser amounts of other products. This example illustrates that a 1:1 $H_2/CO$ ratio is useful in the reaction, although the ratio of 1,3-PDO to other products is not as favorable.

EXAMPLE 22

Eighty grams of tetraglyme, 0.51 gram of $Rh(CO)_2Acac$, 0.55 gram of tricyclohexylphosphine, 1.06 gram of water, and 0.27 gram of 70% aqueous methanesulfonic acid were charged into a 300 cc. autoclave according to the standard procedure. The mixture was pressurized to 1800 psig with a 2:1 $H_2/CO$ gas mixture at ambient room temperature and then quickly heated to 110° C. The resultant mixture was held at this temperature and pressure (110° C. and 2165 psig) for about one hour. Ethylene oxide (11.5 grams) was pressurized into the reactor with 2500 psig 2:1 $H_2/CO$ to initiate the reaction. The reaction was maintained at approximately 110° C. and 2500 psig by heating and adding 2:1 $H_2/CO$ syn gas on demand. It was terminated after 8 hours. Gas chromatographic analysis of the recovered product mixture contained 0.1797 mole of 1,3-PDO, 0.0082 mole acetaldehyde, 0.022 mole ethanol, 0.0068 mole of ethylene glycol, 0.0028 mole acrolein, and 0.0083 mole propanol. This example demonstrates that methanesulfonic acid is useful as an acid source in the reaction.

EXAMPLE 23

Eighty grams of tetraglyme, 0.51 gram $Rh(CO)_2Acac$, 0.41 gram tricyclohexylphosphine, 1.04 gram water, and 1.04 gram lithium iodide were charged into an autoclave according to the standard procedure. The mixture was pressurized to 1800 psig with 2:1 $H_2/CO$ syn gas at ambient room temperature and then quickly heated to 110° C. The resultant mixture was held at this condition (110° C. and 2060 psig) for about one hour. Twelve and three-tenths grams of ethylene oxide was pressurized into the reactor with 2500 psig 2:1 $H_2/CO$ to initiate the reaction. Gas uptake began immediately and the reaction temperature increased instantaneously from 110° to 140° C. The reaction was allowed to run for 1.75 hours at approx. 110° C. and 2500 psig by heating and adding 2:1 $H_2/CO$ on demand. Analysis of the product showed the presence of 0.0733 mole of 1,3-PDO, 0.004 mole of 2-methylpentanal, 0.006 2-methylpentanol, 0.0013 mole acetaldehyde, 0.0364 mole ethanol, 0.0018 mole of ethylene glycol, 0.034 mole propionaldehyde, and 0.0143 mole propanol. This example demonstrates that lithium iodide increases the reaction rate.

EXAMPLE 24

Eighty-nine grams of tetraglyme, 0.51 gram of $Rh(CO)_2Acac$, 0.42 gram of bis(1,2-dicyclohexylphospho)ethane, 1.05 gram of water, 0.23 gram of 85% aqueous phosphoric acid, and 1.04 gram lithium iodide were charged into a 300 cc autoclave according to the standard procedure. The mixture was pressurized to 1800 psig with 2:1 $H_2/CO$ at ambient room temperature and quickly heated to 110° C. The resultant mixture was held at this condition (110° and 2125 psig) for about one hour. Twelve and three-tenths gram of ethylene oxide was pressurized into the reactor with 2500 psig 2:1 $H_2/CO$ gas to initiate the reaction. The reaction was allowed to run for about 1.5 hours at approximately 110° C. and 2500 psig by heating and adding $H_2/CO$ on demand. Analysis of the product showed the presence of 0.1426 mole of 1,3-PDO, 0.001 mole of 3-hydroxypropanal, 0.0003 mole of 2-methylpentanal, 0.0003 mole 3-methylpentanol, 0.0007 mole acetaldehyde, 0.0908 mole ethanol, 0.002 mole propionaldehyde, and 0.0088 mole propanol. This example demonstrates that the bidentate phosphine is similar to the monodentate phosphine in the reaction.

EXAMPLE 25

Eighty grams of tetraglyme, 0.51 gram $Rh(CO)_2Acac$, 0.81 gram tricyclohexylphosphine-HI salt $[HP(C_6H_{11})_3]I$, and 1.064 gram water were charged into an autoclave according to the standard procedure. The mixture was pressurized to 1800 psig with 2:1 $H_2/CO$ syn gas at ambient room temperature and then quickly heated to 110° C. The resultant mixture was held at this condition (110° C. and 2185 psig) for about one hour. Twelve and three-tenths grams of ethylene oxide was pressurized into the reactor with 2500 psig 2:1 $H_2/CO$ to initiate the reaction. The reaction was allowed to run for 5.5 hours at approx. 110° C. and 2500 psig by heating and adding 2:1 $H_2/CO$ on demand. Analysis of the product showed the presence of 0.1636 mole of 1,3-PDO, 0.0024 mole of 2-methylpentanal, 0.0040 mole ethylene oxide, 0.0669 mole ethanol, and 0.0034 mole propanol. This example demonstrates that the phosphonium salt, preformed from a phosphine and an acid, is useful as a catalyst promoter in the reaction.

What is claimed is:

1. A single-step process for manufacturing 1,3-propanediol with CO and $H_2$ in a ether reaction solvent, said process being characterized by reacting a reaction mixture comprising (1) ethylene oxide at a concentration from about 0.01 to about 30 weight percent; (2) rhodium at a molar concentration from about 0.00001 to about 0.1 molar; (3) a phosphine having the formula $$PR_1R_2R_3 \qquad \text{III}$$

wherein $R_1$, $R_2$, and $R_3$ are independently selected, from the group consisting of aliphatic and aromatic hydrocarbon groups, the molar ratio of rhodium to phosphine being from about 10:1 to about 1:10; (4) water in an amount up to about 25 weight percent based on the weight of the reaction mixture; (5) CO; (6) $H_2$; and (7) an acid, the molar ratio of acid to phosphine being from about 10:1 to about 1:10; wherein the molar ratio of CO to $H_2$ is from about 10:1 to about 1:10, and wherein the reaction takes place at a temperature from about 50 to about 200° C. under a pressure from about 200 to about 10,000 psig, for a period of time which is sufficient to form.

2. The process of claim 1 wherein the acid is selected from the group consisting of HI, HCl, methane sulfonic acid and phosphoric acid.

3. The process of claim 1 wherein the solvent is selected from the group consisting of tetraglyme, tetrahydrofuran, and a mixture of glycol polyethers of ethylene and propylene glycols.

4. The process of claim 2 wherein the rhodium is selected from the group consisting of rhodium metal, rhodium oxides, $RhI_3$, $RhBr_3$, $RhCl_3$, $Rh(Acac)_3$, $Rh(CO)_2Acac$, $Rh_6(CO)_{16}$, $[RhCl(CO)_2]_2$, and $Rh(NO_3)_3$.

5. The process of claim 4 wherein the rhodium is present at a concentration from about 0.005 to about 0.10 molar.

6. The process of claim 5 wherein the phosphine is a trialkyl phosphine.

7. The process of claim 6 wherein the phosphine is selected from the group consisting of tri-isopropyl phosphine, tri-sec-butylphosphine, tri-isobutylphosphine, tri-n-butylphosphine, and tri-n-propyl phosphine.

8. The process of claim 1 wherein the molar ratio of rhodium to phosphine is from about 1:2 to about 2:1.

9. The process of claim 8 wherein the molar ratio of acid to phosphine is from about 5:1 to about 1:5.

10. The process of claim 9 wherein the ratio of $H_2:CO$ is from about 5:1 to about 1:1.

11. The process of claim 10 wherein the pressure is from about 1000 to about 3000 psig and the temperature is from about 100 to 130° C.

12. The process of claim 11 wherein the amount of water is up to about 10 weight percent, based on the weight of the reaction mixture.

13. A single-step process for manufacturing 1,3-propanediol with CO and $H_2$ in a ether reaction solvent, said process being characterized by reacting a reaction mixture comprising (1) ethylene oxide at a concentration from about 0.01 to about 30 weight percent; (2) rhodium at a molar concentration from about 0.00001 to about 0.1 molar; (3) a phosphine having the formula $$PR_1R_2R_3 \qquad III$$

wherein $R_1$, $R_2$, and $R_3$ are independently selected from the group consisting of aliphatic and aromatic hydrocarbon groups, the molar ratio of rhodium to phosphine being from about 10:1 to about 1:1; (4) water in an amount from about 0.00 to about 25 weight percent based on the weight of the reaction mixture; (5) CO; (6) $H_2$; wherein the molar ratio of CO to $H_2$ is from about 10:1 to about 1:10, and wherein the reaction takes place at a temperature from about 50 to about 200° C. under a pressure from about 200 to about 10,000 psig, for a period of time which is sufficient to form 1,3-propanediol.

14. The process of claim 13 wherein the solvent is selected from the group consisting of tetraglyme, tetrahydrofuran, and a mixture of glycol polyethers of ethylene and propylene glycols.

15. The process of claim 13 wherein the rhodium is selected from the group consisting of rhodium metal, rhodium oxides, $RhI_3$, $RhBr_3$, $RhCl_3$, $Rh(Acac)_3$, $Rh(CO)_2Acac$, $Rh_6(CO)_{16}$, $[RhCl(CO)_2]_2$, and $Rh(NO_3)_3$.

16. The process of claim 15 wherein the rhodium is present at a concentration from about 0.005 to about 0.10 molar.

17. The process of claim 16 wherein the phosphine is a trialkyl phosphine.

18. The process of claim 17 wherein the phosphine is selected from the group consisting of tri-isopropyl phosphine, tri-sec-butylphosphine, tri-isobutylphosphine, tri-n-butylphosphine, and tri-n-propyl phosphine.

19. The process of claim 18 wherein the molar ratio of rhodium to phosphine is from about 1:2 to about 1:1.

20. The process of claim 19 wherein the ratio of $H_2:CO$ is from about 5:1 to about 1:1.

21. The process of claim 20 wherein the pressure is from about 1000 to about 3000 psig and the temperature is from aobut 100 to 130° C.

22. The process of claim 21 wherein the amount of water is up to about 10 weight percent, based on the weight of solvent.

23. The process of claim 1 wherein a salt of an alkali metal cation is added to the reaction mixture.

24. The process of claim 23 wherein the salt is LiI.

25. The process of claim 23 wherein the salt is lithium acetate.

26. The process of claim 13 wherein a salt of an alkali metal cation is added to the reaction mixture.

27. The process of claim 26 wherein the salt is LiI.

28. The process of claim 27 wherein the salt is lithium acetate.

* * * * *